United States Patent [19]

Kintopf et al.

[11] 4,230,867

[45] Oct. 28, 1980

[54] PROCESS FOR THE PRODUCTION OF 2-ARYL-2H-BENZOTRIAZOLES

[75] Inventors: Siegfried Kintopf; Ulrich Kress, both of Bensheim, Fed. Rep. of Germany

[73] Assignee: Ciba-Geigy Corporation, Ardsley, N.Y.

[21] Appl. No.: 855,040

[22] Filed: Nov. 25, 1977

Related U.S. Application Data

[63] Continuation of Ser. No. 668,344, Mar. 19, 1976, abandoned, which is a continuation-in-part of Ser. No. 577,385, May 14, 1975, abandoned.

[51] Int. Cl.$^3$ ............................................ C07D 249/20
[52] U.S. Cl. ...................................... 548/260; 548/259
[58] Field of Search ..................... 260/308 B; 548/259, 548/260

[56] References Cited

U.S. PATENT DOCUMENTS 3,978,074  8/1976  Jancis ............................... 260/308 B

FOREIGN PATENT DOCUMENTS 48-26012  3/1973  Japan .

*Primary Examiner*—Paul M. Coughlan, Jr.
*Attorney, Agent, or Firm*—Luther A. R. Hall

[57] ABSTRACT

A process for the production of 2-aryl-2H-benzotriazoles comprises reducing and cyclizing the corresponding o-nitroazobenzenes with hydrogen at a temperature in the range of about 20° C. to about 100° C. and at a pressure in the range of about 15 psia (1 atmosphere) to about 1000 psia (66 atmospheres) in an organic solvent mixture containing an organic amine at a pH over 10 in the presence of noble metal hydrogenation catalyst, preferably palladium. High yields of pure product are obtained with a concomitant reduction of undesired by-products and a reduction in effluent pollution problems.

21 Claims, No Drawings

PROCESS FOR THE PRODUCTION OF 2-ARYL-2H-BENZOTRIAZOLES

This application is a continuation of application Ser. No. 668,344, filed on Mar. 19, 1976, now abandoned, which in turn is a continuation-in-part of application Ser. No. 577,385, filed May 14, 1975, now abandoned.

BACKGROUND OF THE INVENTION

This invention pertains to a process for the preparation of 2-aryl-2H-benzotriazoles and derivatives thereof. More particularly, the invention relates to a novel process for preparing 2-aryl-2H-benzotriazoles whereby high yields of the desired products are obtained and effluent pollution problems occurring with present processes for making such products are essentially eliminated.

Heretofore, the conversion of an ortho-nitroazobenzene to the corresponding 2-aryl-2H-benzotriazole has been accomplished by chemical and electrolytic reduction processes. For example, as seen in U.S. Pat. Nos. 3,072,585 and 3,230,194, o-nitroazobenzene derivatives have been chemically reduced utilizing zinc in alcoholic sodium hydroxide solutions to give good yields of the corresponding 2-aryl-2H-benzotriazoles. Ammonium sulfide, alkali sulfides, zinc with ammonia at 80°–100° C., sodium hydrosulfide and zinc with hydrochloric acid have also been used as the chemical reducing agents for this transformation as disclosed in U.S. Pat. No. 2,362,988. The use of ammonium sulfide was also reported by S. N. Chakrabarty et al, *J. Indian Chem. Soc.*, 5, 555 (1928); *Chem. Abst.*, 23, 836, (1929) with mixed results depending on the presence or absence of substituent groups on the 2-aryl group. In some cases the desired 2-aryl-2H-benzotriazoles were not formed at all with the products of reduction being only the corresponding o-aminoazobenzenes.

Electrolytic reduction of o-nitroazobenzenes was reported by H. Itomi, *Mem. Coll. Sci. Kyoto Imp. Univ.*, 12A, No. 6, 343 (1929); *Chem. Abst.*, 24, 2060 (1930) with the use of a copper cathode in dilute sodium hydroxode solution. Yields varied from 25 to 60% depending on specific embodiments and conditions with a major impurity being formed, namely the corresponding o-aminoazobenzene.

The widely used zinc dust and sodium hydroxide chemical reducing system for transforming o-nitroazobenzenes into the corresponding 2-aryl-2H-benzotriazoles was reported by K. Elbs, et al, *J. Prakt. Chem.*, 108, 204 (1924); *Chem. Abst.*, 19, 514 (1925). The yields of the desired 2-aryl-2H-benzotriazoles varied from 30 to 85% depending on the specific o-nitroazobenzene intermediate reduced.

The known chemical and electrolytic reduction processes for preparing 2-aryl-2H-benzotriazoles are not practical or economically attractive in many cases. The widely used zinc dust and sodium hydroxide system produces effluent pollution problems in respect to waste disposal of zinc sludge which is of increasing environmental concern.

The preparation in good yield of the isomeric, but chemically distinct 1H-benzotriazoles by the catalytic reduction in alkaline medium of o-nitrophenylhydrazine and selected phenyl ring substituted alkyl and perfluoroalkyl derivatives thereof was reported in Japanese patent publication, No. Sho 48-26012, Aug. 3, 1973. The isomeric 2H-benzotriazoles of this invention cannot be prepared from phenylhydrazines.

It is therefore an object of this invention to provide a novel process for the preparation of 2-aryl-2H-benzotriazoles avoiding severe pollution and environmental problems.

A further object of this invention is to prepare 2-aryl-2H-benzotriazoles by reducing and cyclizing the corresponding o-nitroazobenzene under certain conditions hereinafter set forth in greater detail whereby high yields of the products can be obtained in acceptable purity.

DETAILED DISCLOSURE

Taken in its broadest aspect, one embodiment of this invention is found in a process for the production of 2-(2-hydroxy-5-methylphenyl)-2H-benzotriazole which comprises reducing and cyclizing 2-nitro-2'-hydroxy-5'-methylazobenzene with hydrogen at reducing conditions in an organic solvent mixture including an organic amine or ammonia in the presence of a hydrogenation catalyst selected from the group consisting of the noble metals of Group VIII of the Periodic Table, and recovering the desired 2-(2-hydroxy-5-methyl)-2H-benzotriazole.

A further embodiment of this invention is found in a process for the production of 2-(2-hydroxy-5-methylphenyl)-2H-benzotriazole which comprises treating 2-nitro-2'-hydroxy-5'-methylazobenzene with hydrogen at a temperature in the range of from about 20° C. to about 100° C. and at a pressure in the range of about 15 psia (1.05 kg/cm$^2$, 1 atmosphere) to about 1000 pounds per square inch (about 70 kg/cm$^2$, 66 atmospheres) in an organic solvent mixture comprising toluene and methanol and including a water-soluble amine, such as diethylamine, in the presence of a hydrogenation catalyst comprising a noble metal of Group VIII of the Periodic Table, removing the noble metal catalyst by filtration, isolating a crude product by distillation, purifying the crude product by removing amine impurities by acid extraction, and recovering the desired 2-(2-hydroxy-5-methylphenyl)-2H-benzotriazole by conventional procedures.

The process of this invention can be carried out at a temperature in the range of from about 20° C. to about 100° C., preferably from about 30° C. to about 80° C., and most preferably from about 40° C. to about 70° C.

A specific embodiment of the invention is exemplified in a process for the production of 2-(2-hydroxy-5-methylphenyl)-2H-benzotriazole, which comprises treating 2-nitro-2'-hydroxy-5'-methylazobenzene with hydrogen at a temperature in the range of from about 20° C. to about 100° C. and at a pressure in the range of from about 15 to about 1000 pounds per square inch (about 1.05 to about 70 kg/cm$^2$) in an organic solvent mixture comprising toluene, methanol and diethylamine in the presence of hydrogenation catalyst comprising palladium composited on charcoal, and recovering the desired 2-(2-hydroxy-5-methylphenyl)-2H-benzotriazole.

A preferred specific embodiment of this invention comprises the reductive cyclization of 2-nitro-2'-hydroxy-5'-methylazobenzene dissolved in a toluene/methanol solution and containing 0.925 equivalents of the water-miscible amine, diethylamine, per mole of the o-nitroazobenzene compound.

With the more difficulty soluble and more hydrocarbon-like members of the 2-aryl-2H-benzotriazoles and the corresponding o-nitroazobenzene starting materials, it is beneficial to employ other organic solvents which can enhance the solubility of said compounds in the reaction mixture. The use of other organic solvents such as isopropanol and additional amounts of organic amines is especially useful with such compounds.

A further preferred specific embodiment of this invention is found in the production of 2-(2-hydroxy-3,5-di-tert-amylphenyl)-2H-benzotriazole by the reductive cyclization of 2-nitro-2'-hydroxy-3',5'-di-tert-amylazobenzene dissolved in isopropanol with 1.1 moles of diethylamine or other organic amine per mole of o-nitroazobenzene starting material.

With these more hydrocarbon-like compounds, the absorption of hydrogen is often considerably above theory indicating that some further reduction of desired product may have occurred.

Other objects and embodiments will be found in the following, further detailed description of this invention.

The reduction of 2-nitro-2'-hydroxy-5'-methylazobenzene was carried out in a mixture of toluene, methanol and diethylamine employing sufficient methanol to assure one liquid phase in the system as two moles of water/mol azobenzene were generated in the system during reduction, and sufficient (about 0.9 moles per mole of azobenzene) diethylamine to provide a strongly alkaline milieu. A hydrogenation catalyst comprising palladium composited on carbon was used and the reduction and cyclization effected at a hydrogen pressure of from about 15 to about 85 pounds per square inch (about 1.05 to about 5.85 kg/cm$^2$, about 1 to about 5.7 atmospheres) at temperatures from about 20° C. to about 100° C., with a recovery of pure product in yields in the order of up to 75%. However, higher pressures up to about 1000 pounds per square inch (about 70 kg/cm$^2$, 66 atmospheres) may also be used with equivalent results.

In like manner, the reduction of 2-nitro-2'-hydroxy-3',5'-di-tert-amylazobenzene was effected in a solution in isopropanol containing at least 1.1 moles of diethylamine per mole of azobenzene to provide the strongly alkaline milieu. A preferred hydrogenation catalyst was palladium composited on alumina.

The catalysts which are employed in the process of this invention for effecting the reduction of o-nitroazobenzenes to form 2-aryl-2H-benzotriazoles comprise metals selected from the noble metals of Group VIII of the Periodic Table, the preferred metal comprising palladium although it is contemplated within the scope of this invention that the other noble metals such as platinum, rhodium, ruthenium, osmium and iridium can also be used, although not necessarily with equivalent results. The metals may be used per se, as their oxides, or in a preferred embodiment of the invention, composited on a solid support such as carbon, silica or alumina. A particularly effective support comprises charcoal or alumina. Very small quantities of catalyst are required to effect the reductive cyclization of this invention. Amounts of noble metal catalyst as low as about 0.001 to 0.005 mol/mol of o-nitroazobenzene to be reduced are effective. More catalyst can be used, but using amounts over 0.01 mol/mol of the o-nitroazobenzene is generally neither needed nor economically attractive.

The noble metal catalysts of this invention can be generally used interchangeably with one another in the instant process. Palladium on asbestos is ineffective in the instant process. However, as intimated above there are some differences between the individual metals. If the o-nitroazobenzene starting material is substituted with a chlorine atom, the use of a palladium catalyst results in the reductive cyclization to the 2-aryl-2H-benzotriazole, but the chlorine atom is also concomitantly cleaved off. However, substitution of palladium by rhodium, the latter which appears to be a milder, more selective catalyst, results in the preparation of the 2-aryl-2H-benzotriazole still containing the chlorine atom. Accordingly, when the preparation of a 2-aryl-2H-benzotriazole containing chlorine on either or both aromatic rings is involved, a rhodium catalyst should be used and the use of a palladium catalyst should be avoided. A preferred catalyst for the reductive cyclization of a 2-nitroazobenzene intermediate substituted with chlorine to the corresponding chlorine substituted 2-aryl-2H-benzotriazole is rhodium composited on charcoal.

A particularly important feature of this invention is the ability of the noble metal catalyst to be used repeatedly to effect the reductive cyclization without appreciable loss in reactivity. As many as 10 batches have been run consecutively with excellent results.

As hereinbefore stated, the reduction is effected at reducing conditions including a temperature within the range of from about 20° C. to about 100° C., a pressure ranging from about 15 to about 1000 pounds per square inch (about 1.05 to about 70 kg/cm$^2$, about 1 to about 66 atmospheres) and with sufficient organic solvent, such as toluene, to keep the starting material and product in solution, water-miscible organic medium, such as methanol, to assure that the water liberated during the reduction is kept in one liquid phase in the system and organic amine, such as diethylamine, to provide a strongly alkaline milieu to permit the desired reaction to occur with minimum of by-product impurities. In the absence of the amine, the desired reaction does not occur.

The organic solvents which may be used in this process to dissolve the o-nitroazobenzene intermediates and corresponding 2-aryl-2H-benzotriazoles can be non-polar hydrocarbon solvents such as benzene, toluene, xylene, cyclohexane, aliphatic hydrocarbons, such as hexane, heptane, petroleum mineral spirits, and other hydrocarbon materials and mixtures thereof. For reasons of economy, ease of operation and availability, toluene is particularly useful in the process of this invention.

Since water is liberated during the reductive cyclization reaction, it is necessary that a water-miscible solvent or cosolvent be used in the process of this invention in order to keep everything except the dispersed catalyst in one liquid phase. This is particularly needed when the non-polar solvents described above are employed. Water-miscible solvents or cosolvents useful in this invention include the water-miscible alcohols such as methanol, ethanol, isopropanol, n-propanol, n-butanol and methyl cellosolve (2-methoxyethanol). Particularly useful are methanol when used with non-polar cosolvents or isopropanol when used alone.

Other water-miscible solvents or cosolvents useful in this process include ethers such as tetrahydrofuran, 1,4-dioxane, 1,2'-dimethoxyethane, 1,2'-diethoxyethane and the like.

Other solvents found useful in this process include the trialkyl phosphates such as triethyl phosphate, tributyl phosphate and the like.

The reductive cyclization of o-nitroazobenzenes to the corresponding 2-aryl-2H-benzotriazoles in the process of this invention requires the presence of a strongly alkaline milieu. In the absence of an organic amine or ammonia, the desired reaction does not take place. Organic amines useful in the process of this invention are preferably water-miscible for the reasons given above although other amines may also be used provided sufficient water-miscible solvent or cosolvent is present. Organic amines useful in this process include the primary, secondary or tertiary aliphatic amines with alkyl groups of 1 to 6 carbon atoms, piperidine, piperazine, morpholine, pyrrolidine, guanidine and the like. For reasons of economy, ease of operation and availability, morpholine, piperidine, and the lower dialkylamines such as diethylamine, dimethylamine, di-n-propylamine and the like are preferred. Particularly preferred is diethylamine.

While the reduction cyclization reaction does not occur in the absence of a strong alkaline milieu such as is provided by one or more of the organic amines described above, it is often expedient to run the instant process where the organic solvent consists essentially entirely of one of the organic amines alone. In such a case, an excess molar quantity of amine relevant to the o-nitroazobenzene is always present. This solvent system has the advantage of simplified solvent recovery at the end of the reaction since mixtures of solvents are not involved. Amines providing a particularly good balance of base strength, solvent character, physical properties, ease of handling, availability and operability in the instant process include n-propylamine, diethylamine, triethylamine, isopropylamine, n-butylamine, dibutylamine, tert-butylamine, amylamine, morpholine and the like.

The reductive cyclization reaction may be carried out under a variety of concentrations of solvents, cosolvents and organic amines.

The amount of organic amine which must be used in the process of this invention is at least 0.1 moles of amine per mole of o-nitroazobenzene intermediate and preferably at least 0.9 moles per mole of o-nitroazobenzene intermediate. Additional quantities of organic amine may be used, but employing amounts over 1.5 moles/mole of o-nitroazobenzene is not necessary.

The concentrations by weight of o-nitroazobenzene intermediate in the organic solvent system can range from dilute solutions in the range of 5–10% to concentrated solutions in the range of 20–30%. For reasons of economy, the more concentrated solutions are preferred.

The organic solvent system useful in this process can comprise 100% of a water-miscible organic alcohol or ether without the presence of any non-polar cosolvent. These systems can also comprise a mixture of a non-polar organic solvent with a water-miscible organic cosolvent where the maximum amount of non-polar solvent by weight in the total solvent system is in the range of 65 to 75%.

With many of the 2-aryl-2H-benzotriazoles of this invention, a toluene/methanol/diethylamine mixture is preferred partially because of fortuitous combination of boiling points allow their convenient recovery by distillation for recycling in the subsequent reaction runs. When using this organic solvent mixture, it is possible at the end of the reduction and cyclization reaction to remove the catalyst by filtration for further recycling which is a special feature of this process while leaving the desired 2-aryl-2H-benzotriazole product in organic solution.

Isolation of a product in good yield and acceptable purity is another feature of this invention. The organic solution of the desired 2-aryl-2H-benzotriazole after removal of the noble metal catalyst by filtration is subjected to distillation to remove the organic solvents and small amount of water formed during the reduction to give a crude product in the range of 75 to 85% yield, but which contains some amine by-product impurities. The crude product may conveniently be purified by redissolving in toluene, extracting the amine impurities by aqueous mineral acid, preferably 70% sulfuric acid, and isolating by conventional procedures to give purified products of high purity in yields in the range of 70 to 80%. A variety of trace by-products are formed during the reduction of o-nitroazobenzenes. These include the corresponding o-aminoazobenzenes, o-aminohydrazobenzenes, o-phenylenediamine, anilines, aminophenols and 1,2,3-benzotriazoles. Most of these by-product impurities are removed by the acid, preferably sulfuric acid, wash.

With 2-aryl-2H-benzotriazoles such as 2-(2-hydroxy-3,5-di-tert-amylphenyl)-2H-benzotriazole, the crude products are obtained in yields in the range of 52–67%, and these materials may contain somewhat larger amounts of amine by-products than those such as 2-(2-hydroxy-5-methylphenyl)-2H-benzotriazole. However, these amine by-products are also removed as hereinbefore stated by dissolving the crude product in an organic solvent such as petroleum mineral spirits, extracting with aqueous mineral acid, and isolating the desired products of high purity by conventional procedures in good yields.

The process of this invention may be effected in any suitable manner and may comprise either a batch or continuous type of operation. For example, when a batch-type operation is used, a quantity of the hydroxy-substituted o-nitroazobenzene, toluene, methanol, diethylamine along with the catalyst such as palladium composited on charcoal, is placed in an appropriate apparatus such as a shaking or stirred autoclave. Hydrogen is pressurized in until the desired initial pressure is reached. The autoclave and the contents thereof are then heated, if needed, to the desired reaction temperature and maintained thereat with agitation until the theoretical amount of hydrogen is absorbed whereupon no further hydrogen is taken up and the reduction reaction is complete. At the end of this time the excess pressure is vented, the solution, usually warm, is subjected to filtration, preferably under an inert atmosphere such as nitrogen or argon, to remove the catalyst. The solution is then subjected to distillation to yield the crude product which may be further purified by dissolving in toluene, extraction with aqueous acid and recrystallization from an organic solvent.

It is also contemplated within the scope of this invention that the preparation of the 2-aryl-2H-benzotriazoles by the reduction and cyclization of o-nitroazobenzenes may also be effected in a continuous manner, although not necessarily with equivalent results. For example, when a continous type operation is used, the hydroxy-substituted o-nitroazobenzene starting material is premixed with, and dissolved in an organic solvent mixture containing a water soluble amine, said mixture fed continuously to a reaction zone which is maintained at the proper operating conditions of temperature and pressure and which contains the hydrogenation catalyst. Hydrogen is pressurized into the reaction zone by a separate means. After a desired residence time, the reactor effluent is continuously discharged and the effluent solution is distilled to isolate the desired product. Due to the nature of the catalyst employed, a particularly effective continuous type of operation comprises a fixed bed of catalyst subjected to either an upward or downward flow of the reaction solution. If it is desirable to carry out the reduction as a two-step process with a different operating temperature for each step, two reaction zones in series each operating at the preferred temperature range for the specific reduction step involved may be used.

The reduction of o-nitroazobenzenes to the corresponding 2-aryl-2H-benzotriazoles is a two-step process as outlined below.

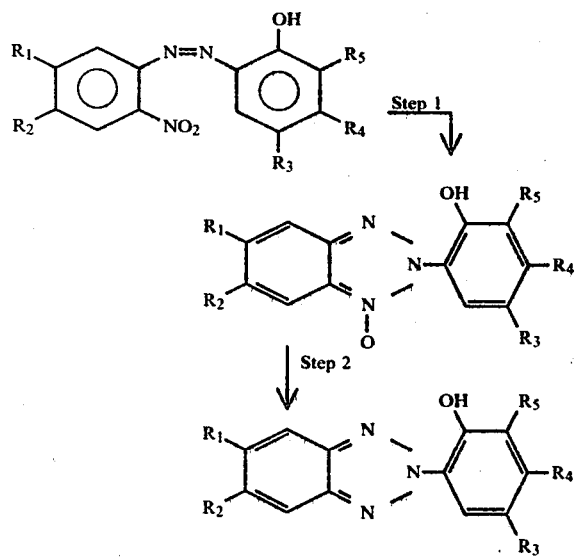

Step 1

The reduction of the o-nitroazobenzene to the N-oxybenzotriazole derivative proceeds rapidly and exothermically even at low temperature under the process conditions of this invention.

Step 2

The reduction of the N-oxybenzotriazole intermediate to the corresponding 2-aryl-2H-benzotriazole product goes more slowly. This reduction can be greatly expedited by adding more catalyst, raising the temperature, increasing the hydrogen pressure or by combination of these factors.

Generally, the reaction ceases when the N-oxy intermediate is completely reduced to the corresponding 2-aryl-2H-benzotriazole making for facile control of this catalytic hydrogenation process. However, with some highly substituted benzotriazoles, reduction should be stopped when the appropriate amount of hydrogen has been absorbed and reacted to prevent further reductive cleavage of the desired 2-aryl-2H-benzotriazoles prepared.

Specifically, the instant invention provides an improved process for production of compounds having the formula I

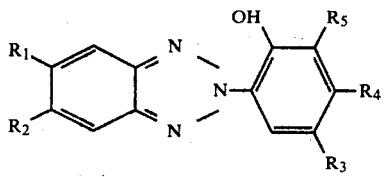

wherein
$R_1$ is hydrogen or chlorine,
$R_2$ is hydrogen, chlorine, lower alkyl of 1 to 4 carbon atoms, lower alkoxy of 1 to 4 carbon atoms, carboalkoxy of 2 to 9 carbon atoms, carboxy or —$SO_3H$,
$R_3$ is alkyl of 1 to 12 carbon atoms, alkoxy of 1 to 4 carbon atoms, phenyl, phenyl substituted with alkyl groups, said alkyl groups having 1 to 8 carbon atoms, cycloalkyl of 5 to 6 carbon atoms, carboalkoxy of 2 to 9 carbon atoms, chlorine, carboxyethyl or arylalkyl of 7 to 9 carbon atoms,
$R_4$ is hydrogen, lower alkyl of 1 to 4 carbon atoms, lower alkoxy of 1 to 4 carbon atoms, chlorine or hydroxyl, and
$R_5$ is hydrogen, alkyl of 1 to 12 carbon atoms, chlorine, cycloalkyl of 5 to 6 carbon atoms or arylalkyl of 7 to 9 carbon atoms.

$R_2$ can be lower alkyl of 1 to 4 carbon atoms such as methyl, ethyl or n-butyl. $R_2$ can also be lower alkoxy of 1 to 4 carbon atoms such as methoxy, ethoxy or n-butoxy. $R_2$ can also be carboalkoxy of 2 to 9 carbon atoms such as carbomethoxy, carboethoxy, or carbo-n-octoxy.

$R_3$ can be alkyl of 1 to 12 carbon atoms such as methyl, ethyl, sec-butyl, tert-butyl, amyl, tert-octyl or n-dodecyl. $R_3$ can also be alkoxy of 1 to 4 carbon atoms such as methoxy, ethoxy or n-butoxy. $R_3$ is also phenyl substituted with alkyl groups, said alkyl groups having 1 to 8 carbon atoms such as methyl, tert-butyl, tert-amyl or tert-octyl. $R_3$ can also be cycloalkyl of 5 to 6 carbon atoms such as cyclopentyl or cyclohexyl. $R_3$ is also carboalkoxy of 2 to 9 carbon atoms such as carbomethoxy, carboethoxy, carbo-n-butoxy or carbo-n-octoxy. $R_3$ is also arylalkyl of 7 to 9 carbon atoms such as benzyl, α-methylbenzyl or α,α-dimethylbenzyl.

$R_4$ can be lower alkyl of 1 to 4 carbon atoms such as methyl, ethyl or n-butyl.

$R_4$ can also be lower alkoxy of 1 to 4 carbon atoms such as methoxy, ethoxy or n-butyloxy.

$R_5$ can be alkyl of 1 to 12 carbon atoms such as methyl, sec-butyl, tert-butyl, tert-amyl, tert-octyl or n-dodecyl.

$R_5$ can also be cycloalkyl of 5 to 6 carbon atoms such as cyclopentyl or cyclohexyl. $R_5$ is also arylalkyl of 7 to 9 carbon atoms such as benzyl, α-methylbenzyl or α,α-dimethylbenzyl.

Preferably $R_1$ is hydrogen.
Preferably $R_2$ is hydrogen, chlorine, lower alkyl of 1 to 2 carbon atoms, methoxy or carboxy.
Preferably $R_3$ is alkyl of 1 to 12 carbon atoms cyclohexyl, phenyl, chlorine, α-methylbenzyl or carboxyethyl.
Preferably $R_4$ is hydrogen, hydroxyl or methyl.
Preferably $R_5$ is hydrogen, chlorine, alkyl of 1 to 12 carbon atoms, cyclohexyl, benzyl or α-methylbenzyl.
Most preferably $R_2$ is hydrogen or chlorine.
Most preferably $R_3$ is methyl, tert-butyl, tert-amyl, tert-octyl, sec-butyl, cyclohexyl, chlorine or carboxyethyl.

Most preferably $R_4$ is hydrogen.

Most preferably $R_5$ is hydrogen, chlorine, methyl, sec-butyl, tert-butyl, tert-amyl, tert-octyl or α-methylbenzyl.

The process involved the reduction of an o-nitroazobenzene intermediate of the formula II

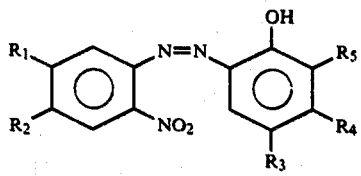

wherein $R_1$, $R_2$, $R_3$, $R_4$ and $R_5$ are as described previously.

The starting o-nitroazobenzene intermediates are prepared by coupling the appropriate o-nitrobenzenediazonium compounds of formula III

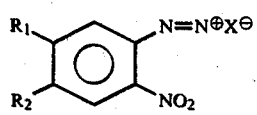

wherein $R_1$ and $R_2$ are as described previously and X is chloride, sulfate, or other anionic species, but preferably chloride, with phenols of formula IV

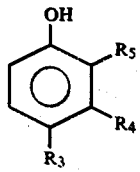

which couple in the ortho position to the hydroxy group.

The o-nitrobenzenediazonium compounds are in turn prepared by standard diazotization procedures using sodium nitrite in acid solution with the corresponding o-nitroanilines of formula V

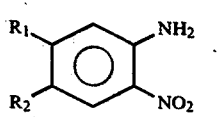

For illustration purposes some specific examples of compounds of formulas IV and V are listed. These items are generally available as items of commerce.

Compounds of Formula IV
p-cresol
2,4-di-tert-butylphenol
2,4-di-tert-amylphenol
2,4-di-tert-octylphenol
2-tert-butyl-4-methylphenol
4-cyclohexylphenol
4-tert-butylphenol
4-tert-amylphenol
4-tert-octylphenol
2,4-dimethylphenol
3,4-dimethylphenol
4-chlorophenol
2,4-dichlorophenol
3,4-dichlorophenol
4-phenylphenol
4-phenoxyphenol
4-o-tolylphenol
4-(4'-tert-octyl)phenylphenol
ethyl 4-hydroxybenzoate
n-octyl 4-hydroxybenzoate
4-methoxyphenol
4-n-octylphenol
4-n-dodecylphenol
resorcinol
4-(α-methylbenzyl)phenol
2-(α-methylbenzyl)-4-methylphenol
2-cyclohexyl-4-methylphenol
4-sec-butylphenol
2-sec-butyl-4-tert-butylphenol
2-tert-butyl-4-sec-butylphenol
4-carboxyethylphenol
2-methyl-4-carboxyethylphenol Preferably compounds of formula IV useful in this invention are
p-cresol
2,4-di-tert-butylphenol
2,4-di-tert-amylphenol
2,4-di-tert-octylphenol
2-tert-butyl-4-methylphenol
4-tert-octylphenol
4-n-octylphenol
4-n-dodecylphenol
resorcinol
2-sec-butyl-4-tert-butylphenol
2-(α-methylbenzyl)-4-methylphenol Compounds of Formula V
o-nitroaniline
4-chloro-2-nitroaniline
4,5-dichloro-2-nitroaniline
4-methoxy-2-nitroaniline
4-methyl-2-nitroaniline
4-ethyl-2-nitroaniline
n-butyl 3-nitro-4-aminobenzoate
n-octyl 3-nitro-4-aminobenzoate
4-n-butoxy-2-nitroaniline
3-nitro-4-aminobenzoic acid
3-nitro-4-aminobenzenesulfonic acid Preferably compounds of formula V useful in this invention are
o-nitroaniline
4-chloro-2-nitroaniline The 2-aryl-2H-benzotriazoles have found wide use as dyestuff intermediates, optical brightner blue fluorescent agents and selective ultraviolet light absorbing stabilizers affording valuable protection for fibers, films and a variety of polymeric structures subject to deterioration by ultraviolet radiation. These materials have become important items of commerce.

The 2-aryl-2H-benzotriazoles are complex organic molecules which require careful synthetic procedures for their production in good yield and acceptable purity.

The present invention is concerned with an improved process to prepare ultraviolet stabilizers which are substituted 2-aryl-2H-benzotriazoles. These are distinguished by a very slight absorption in visible light and very high fastness to light in various substrates. Particularly valuable members of these stabilizers are compounds having a free hydroxyl group in the 2-position of the aryl group linked to the 2-nitrogen of the benzotriazole and which are further substituted in the 3- and 5- or in the 4- and 5-positions by lower alkyl groups and may be substituted by a chlorine in the 5-position of the benzotriazole nucleus.

The description, preparation and uses of these valuable substituted 2-aryl-2H-benzotriazoles are further taught in the U.S. Pat. Nos. 3,004,896, 3,055,896, 3,072,585, 3,074,910, 3,189,615 and 3,230,194.

The following examples are given to illustrate the process of the present invention, but are not intended to limit the scope of the present invention in any manner whatsoever.

EXAMPLE 1

2-(2-Hydroxy-5-methylphenyl)-2H-benzotriazole

To a 1-liter, low pressure hydrogenation reactor were charged under nitrogen at room temperature 20 grams of 2-nitro-2'-hydroxy-5'-methylazobenzene (95% pure) dissolved in 55 grams of toluene, 25 grams of methanol and 5 grams of diethylamine and 1.5 grams of 5% palladium on charcoal hydrogenation catalyst slurried in the aforementioned organic solvents. The amount of catalyst is 7.5% based on the azobenzene intermediate and the molar ratio of diethylamine to azobenzene intermediate is 0.925. The reactor was flushed several times with hydrogen and then pressurized to 15 psia (1.05 kg/cm$^2$, 1 atmosphere) with hydrogen. External cooling was provided to prevent the temperature of the reactor contents from exceeding 35° C. during the exothermic first step of the reduction. The first step was complete in 15 minutes when fresh catalyst was used or in 30 minutes when the catalyst 4 times recycled was used.

The second step of the reduction of the N-oxy benzotriazole to the desired 2-aryl-2H -benzotriazole was carried out at a temperature of 50° C. This step is not extremely exothermic and some external heating was required in the latter stages of the reduction. The second step was complete in another 30 minutes when fresh catalyst was used or in another 60 minutes when catalyst 4 times recycled was employed.

When hydrogen absorption ceased and the reaction was complete, the hydrogen remaining in the reactor was now vented and a nitrogen atmosphere was reimposed on the reactor contents.

The reactor contents were then filtered under nitrogen to remove the palladium on charcoal catalyst dispersed therein. The recovered catalyst was washed on the filter with toluene. This washed catalyst was then ready for recycling in the hydrogenation process where it could be used for many additional cycles with minimum loss in catalyst activity.

The combined alkaline organic solution of the desired product was then concentrated by distillation under vacuum to give as distillates toluene-methanol, toluene-diethylamine and finally toluene-water. From the latter, water can be separated. The recovered solvents can then be recycled to another hydrogenation reaction. The still pot residue comprises the crude product in a yield of grams (80% of theory). The crude product contains some amine by-product which can be removed by acid extraction.

The crude product was purified by dissolving 8.0 grams of the crude product in 11.0 grams of toluene. This solution was extracted with 8.0 grams of 70% aqueous sulfuric acid. The toluene solution was then stirred with 0.8 grams of Prolit Rapid, an acidic clay, which was removed then by filtration. The clay was washed with 3.0 grams of toluene. The combined toluene filtrate was then concentrated by vacuum distillation. After 9.0 grams of toluene was isolated, 6.5 grams of isopropanol was added dropwise to the still-pot residue. The resulting solution was then cooled to 0°-5° C. and the resulting crystals were isolated by filtration, washed with 4.0 grams of cold isopropanol and vacuum dried at 70°-80° C. The yield of pure product was 7.6 grams (75% of theory based on the original azobenzene intermediate).

EXAMPLE 2

2-(2-Hydroxy-5-methylphenyl)-2H-benzotriazole

When using the procedure of Example 1, the hydrogen pressure employed was in the range of 50-30 psia (3.5-2.1 kg/cm$^2$, 3.3-2 atmospheres) instead of 15 psia (1.05 kg/cm$^2$, 1 atmosphere), the reaction temperature was held at 58°-60° C. rather than 35° C. for the first step and 50° C. for the second step and only 3% by weight of 5% palladium on charcoal catalyst was used instead of 7.5% by weight based on azobenzene intermediate, the reaction time for total absorption of hydrogen was 125 minutes. The yield of crude product was nearly the same, namely 75% of theory.

When in Example 2, the hydrogen pressure employed was 15 psia (1.05 kg/cm$^2$, 1 atmosphere), the reaction time was extended to 250 minutes, but the yield of crude product was the same (75% of theory).

If in Example 2, the diethylamine component of the organic solvent system was left out, complete absorption of hydrogen occurred in 60 minutes, but none of the desired product was obtained. The presence of the organic base, such as diethylamine, is essential for the process to yield the desired 2-aryl-2H-benzotriazoles upon reduction of the corresponding o-nitroazobenzenes.

EXAMPLE 3

2-(2-Hydroxy-5-methylphenyl)-2H-benzotriazole

If in Example 2, the 5% palladium on charcoal catalyst was replaced by an equivalent amount of 5% platinum on charcoal catalyst and the reaction carried out at a temperature in the range of 58°-78° C., the reaction time for complete absorption of hydrogen was 50 minutes, and the yield of crude desired product was 55%.

Platinum is an operative catalyst for this hydrogenation, but is less selective than palladium giving rise to more undesired by-products.

If in Example 3, the diethylamine component of the organic solvent system was left out, complete absorption of hydrogen occurred in 60 minutes, but no desired product was obtained. Thus, it is essential for the organic solvent system to contain a base such as an organic amine for the process to be operable to produce 2-aryl-2H-benzotriazoles.

EXAMPLE 4

2-(2-Hydroxy-5-methylphenyl)-2H-benzotriazole

If in Example 2, the 5% palladium on charcoal catalyst is replaced by an equivalent amount of 5% rhodium on charcoal catalyst, the crude desired product is obtained.

If Example 4, the diethylamine component of the organic solvent system was left out, complete absorption of hydrogen occurred in 90 minutes, but no desired product was obtained.

As with both the palladium and platinum catalysts, no product was obtained with the rhodium on charcoal catalyst with the organic solvent system in the absence of a base such as diethylamine.

EXAMPLE 5

2-(2-Hydroxy-3,5-di-tert-amylphenyl)-2H-benzotriazole

When using the general procedure of Example 1, an equivalent amount of 2-nitro-2'-hydroxy-3',5'-di-tert-amylazobenzene was substituted for 2-nitro-2'-hydroxy-5'-methylazobenzene, the above noted product was obtained in yields ranging from 52 to 67% based on the original azobenzene intermediate used. The reaction was carried out in a 23.3% by weight solution of the azobenzene in isopropanol with 1 to 3% by weight of catalyst and with 1.1 to 2.0 moles of diethylamine per mole of azobenzene intermediate.

The effect of the quantity of water-miscible organic amine on the yield of 2-aryl-2H-benzotriazole is seen from Table A. At least 1.1 moles of organic amine per mole of o-nitroazobenzene is required to give good yields of the desired product. Using more than 1.5 moles organic amine per mole of o-nitroazobenzene intermediate did not further enhance product yields.

TABLE A

Effect of Quantity of Diethylamine on Yield of 2-(2-Hydroxy-3,5-di-tert-amylphenyl)-2H-benzotriazole*

| Hydrogen Absorbed % of Theory | Equivalents Amine to o-Nitroazobenzene | % Yield of 2-Aryl-2H-benzotriazole |
|---|---|---|
| 143 | 0.1 | 24.7 |
| 155 | 1.1 | 55.0 |
| 154 | 1.5 | 49.5 |
| 156 | 2.0 | 50.0 |

*Reaction conditions:
23.3% by weight solution of corresponding o-nitroazobenzene intermediate in isopropanol.
atmospheric pressure
temperature range 55°-60° C.
catalyst 5% palladium-on-charcoal used at 3% by weight of o-nitroazobenzene intermediate In Table B are shown the effect of other variables on the yields of 2-(2-hydroxy-3,5-di-tert-amylphenyl)-2H-benzotriazole prepared by the reductive cyclization of 23.3% by weight solution of the corresponding o-nitroazobenzene intermediate in isopropanol using 5% palladium catalysts composited on various substrates, using various concentrations of said catalysts and various temperatures in the presence of 2 moles of diethylamine per mole of o-nitroazobenzene intermediate run at atmospheric pressure.

TABLE B

| Reaction Temperature °C. | 5% Pd on Substrate | Weight Conc % of Catalyst based on Azo Inter. | Hydrogen Absorbed % of Theory | % Yield 2-Aryl-2H-benzotriazole |
|---|---|---|---|---|
| 60 | Carbon | 1 | 152 | 52 |
| 60 | Carbon | 2 | 142 | 62 |
| 45 | Alumina | 1 | 134 | 67 |
| 45 | Carbon | 1 | 142 | 57 |
| 45 | Asbestos | 2 | 83 | Stopped at N-oxy |
| 45 | Carbon | 2 | 134 | 64 |

The yields of the 2-aryl-2H-benzotriazole varied from 52 to 67%. A lower temperature (45° C. versus 60° C.), higher concentration of catalyst (2% versus 1%), and the use of alumina rather than carbon as the carrier for the palladium catalyst appeared to be marginally beneficial. In all of these runs, the products contained some 2-amino-2'-hydroxy-3',5'-di-tert-amylhydrazobenzene as an undesired by-product accounting for some lower yields (52-67%) with this particular 2-aryl-2H-benzotriazole compared to the yields of 75-85% contained with 2-(2-hydroxy-5-methylphenyl)-2H-benzotriazole.

EXAMPLE 6

2-(2-Hydroxy-5-tert-octylphenyl)-2H-benzotriazole

When using the procedure of Example 1 an equivalent amount of 2-nitro-2'-hydroxy-5'-tert-octylazobenzene is substituted for 2-nitro-2'-hydroxy-5'-methylazobenzene, the above noted product is obtained.

EXAMPLE 7

5-Chloro-2-(2-hydroxy-3,5-di-tert-butylphenyl)-2H-benzotriazole

When in Example 5, the 2-nitro-2'-hydroxy-3',5'-di-tert-amylazobenzene was replaced by an equivalent amount of 2-nitro-5-chloro-2'-hydroxy-3',5'-di-tert-butylazobenzene and the 5% palladium on charcoal catalyst was replaced by an equivalent amount of 5% rhodium on charcoal catalyst, the above noted product was obtained.

If the 5% palladium on charcoal catalyst was used, the resulting product was the deschloro compound 2-(2-hydroxy-3,5-di-tert-butylphenyl)-2H-benzotriazole.

EXAMPLE 8

5-Chloro-2-(2-hydroxy-3-tert-butyl-5-methylphenyl)-2H-benzotriazole

When in Example 5, the 2-nitro-2'-hydroxy-3',5'-di-tert-amylazobenzene is replaced by an equivalent amount of 2-nitro-5-chloro-2'-hydroxy-3'-tert-butyl-5'-methylazobenzene and the 5% palladium on charcoal catalyst by a like amount of 5% rhodium on charcoal catalyst, the above noted product is obtained.

EXAMPLE 9

2-(2-Hydroxy-3,5-di-tert-butylphenyl)-2H-benzotriazole

When using the general procedure of Example 5, a 23% by weight suspension of 2-nitro-2'-hydroxy-3',5'-di-tert-butylazobenzene in isopropanol/triethylamine (1/0.18) was hydrogenated at 45° C. at 1 atmosphere pressure for 3 hours in the presence of 3% of a 5% palladium on charcoal catalyst the above noted product was obtained in a yield of 77%.

EXAMPLE 10

2-(2-Hydroxy-5-methylphenyl)-2H-benzotriazole

When using the general procedure of Example 1 the organic solvent toluene was replaced by a trialkyl phosphate, the above noted product was obtained in good yield.

A suspension of 23.3 grams of 2-nitro-2'-hydroxy-5'-methylazobenzene in 80 grams of tributyl phosphate, 20 grams of methanol and 8 grams of diethylamine with 1.5 grams of 5% palladium on charcoal catalyst was hydrogenated at 1 atmosphere for 55 minutes at a maximum temperature of 55° C. The above noted product with a melting point of 129°-130° C. was obtained in a yield of 80%.

When using the procedure listed above the tributyl phosphate was replaced by a like amount of triethyl phosphate and with no methanol being present, the above noted product (melting point 128°-130° C.) was obtained in a yield of 76%.

EXAMPLE 11

2-(2-Hydroxy-5-methyl)-2H-benzotriazole

When using the general procedure of Example 1 the toluene, methanol and diethylamine organic solvent mixture is replaced by a comparable weight of n-propylamine, the above noted product is obtained.

EXAMPLE 12

2-(2-Hydroxy-3,5-di-tert-amylphenyl)-2H-benzotriazole

When using the general procedure of Example 5 the isopropanol and diethylamine organic solvent mixture is replaced by a comparable weight of morpholine, the above noted product is obtained.

What is claimed is:

1. A process for the production of 2-aryl-2H-benzotriazoles of the formula I

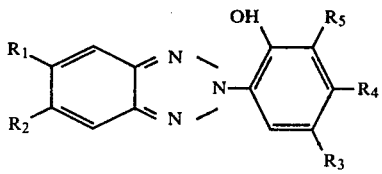

wherein
$R_1$ is hydrogen or chlorine,
$R_2$ is hydrogen, chlorine, lower alkyl of 1 to 4 carbon atoms, lower alkoxy of 1 to 4 carbon atoms, carboalkoxy of 2 to 9 carbon atoms, carboxy or $-SO_3H$,
$R_3$ is alkyl of 1 to 12 carbon atoms, alkoxy of 1 to 4 carbon atoms, phenyl, phenyl substituted with alkyl groups, said alkyl groups having 1 to 8 carbon atoms, cycloalkyl of 5 to 6 carbon atoms, carboalkoxy of 2 to 9 carbon atoms, chlorine, carboxyethyl or phenylalkyl of 7 to 9 carbon atoms,
$R_4$ is hydrogen, lower alkyl of 1 to 4 carbon atoms, lower alkoxy of 1 to 4 carbon atoms, chlorine or hydroxyl, and
$R_5$ is hydrogen, alkyl of 1 to 12 carbon atoms, chlorine, cycloalkyl of 5 to 6 carbon atoms or phenylalkyl of 7 to 9 carbon atoms,
which comprises
reducing and cyclizing the corresponding o-nitroazobenzene

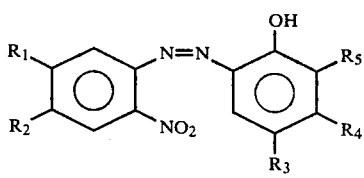

with hydrogen at a temperature in the range of from about 20° C. to about 100° C. and at a pressure in the range of from about 15 psia (1.05 kg/cm$^2$, 1 atmosphere) to about 1000 psia (70 kg/cm$^2$, 66 atmospheres) while mixed in an alkaline organic solvent mixture comprising an organic amine in a concentration of at least 0.1 mole of amine per mole of o-nitroazobenzene in the presence of hydrogenation catalyst selected from the group consisting of the noble metals of Group VIII of the Periodic Table with the proviso that the hydrogenation catalyst cannot be palladium-on-asbestos, and with the proviso that, when $R_1$, $R_2$, $R_3$, $R_4$ or $R_5$ is chlorine, the hydrogenation catalyst cannot be palladium,
separating the catalyst which is suitable for recycle, and recovering the desired 2-aryl-2H-benzotriazole.

2. A process according to claim 1 which further comprises
removing the noble metal catalyst by filtration,
distilling the organic solvent to recover the crude product, and
purifying the crude product by removing amine impurities by acid extraction.

3. A process according to claim 1 wherein the hydrogenation catalyst is selected from the group consisting of palladium, platinum and rhodium, and the organic solvent mixture consists of a water-miscible organic alcohol or ether, optionally containing non-polar hydrocarbon solvent, with at least 0.1 mole of organic amine per mole of o-nitroazobenzene being reduced and cyclized.

4. A process according to claim 3 wherein the organic solvent mixture comprises toluene and methanol and the organic amine is diethylamine.

5. A process according to claim 3 wherein the organic solvent comprises isopropanol and the organic amine is diethylamine.

6. A process according to claim 3 wherein at least 0.9 mole of organic amine per mole of o-nitroazobenzene is used.

7. A process according to claim 1 wherein the hydrogenation catalyst is palladium.

8. A process according to claim 7 characterized in that said palladium is composited on charcoal or alumina.

9. A process according to claim 7 for the production of a compound of formula I wherein
$R_1$ is hydrogen,
$R_2$ is hydrogen, lower alkyl of 1 to 2 carbon atoms, methoxy or carboxy,
$R_3$ is alkyl of 1 to 12 carbon atoms, cyclohexyl, phenyl, α-methylbenzyl or carboxyethyl,
$R_4$ is hydrogen, hydroxyl or methyl, and
$R_5$ is hydrogen, alkyl of 1 to 12 carbon atoms, cyclohexyl, benzyl or α-methylbenzyl.

10. A process according to claim 7 for the production of a compound of formula I wherein
$R_1$ is hydrogen,
$R_2$ is hydrogen,
$R_3$ is methyl, sec-butyl, tert-butyl, tert-amyl, tert-octyl, cyclohexyl or carboxyethyl,
$R_4$ is hydrogen, and
$R_5$ is hydrogen, methyl, tert-butyl, sec-butyl, tert-amyl, tert-octyl or α-methylbenzyl.

11. A process according to claim 7 for the production of 2-(2-hydroxy-5-methylphenyl)-2H-benzotriazole.

12. A process according to claim 7 for the production of 2-(2-hydroxy-5-tert-octylphenyl)-2H-benzotriazole.

13. A process according to claim 7 for the production of 2-(2-hydroxy-3,5-di-tert-amylphenyl)-2H-benzotriazole.

14. A process according to claim 1 wherein the hydrogenation catalyst is rhodium.

15. A process according to claim 14 characterized in that said rhodium is composited on charcoal.

16. A process according to claim 14 for the production of a compound of formula I wherein
 $R_1$ is hydrogen,
 $R_2$ is hydrogen, chlorine, lower alkyl of 1 to 2 carbon atoms, methoxy or carboxy,
 $R_3$ is alkyl of 1 to 12 carbon atoms, cyclohexyl, phenyl, chlorine, α-methylbenzyl or carboxyethyl,
 $R_4$ is hydrogen, hydroxyl or methyl, and
 $R_5$ is hydrogen, alkyl of 1 to 12 carbon atoms, chlorine, cyclohexyl, benzyl or α-methylbenzyl.

17. A process according to claim 14 for the production of a compound of formula I wherein
 $R_1$ is hydrogen,
 $R_2$ is hydrogen or chlorine,
 $R_3$ is methyl, sec-butyl, tert-butyl, tert-amyl, tert-octyl, methoxy, cyclohexyl, chlorine or carboxyethyl,
 $R_4$ is hydrogen, and
 $R_5$ is hydrogen, chlorine, methyl, tert-butyl, sec-butyl, tert-amyl, tert-octyl or α-methylbenzyl.

18. A process according to claim 14 for the production of 5-chloro-2-(2-hydroxy-3,5-di-tert-butylphenyl)-2H-benzotriazole.

19. A process according to claim 14 for the production of 5-chloro-2-(2-hydroxy-3-tert-butyl-5-methylphenyl)-2H-benzotriazole.

20. A process according to claim 1 wherein the hydrogenation catalyst is selected from the group consisting of palladium, platinum and rhodium, and the organic solvent consists essentially of an organic aliphatic or alicyclic amine or morpholine.

21. A process according to claim 1 wherein the organic amine is selected from the group consisting of primary aliphatic amines with alkyl groups of 1 to 6 carbon atoms, secondary aliphatic amines with alkyl groups of 1 to 6 carbon atoms, tertiary aliphatic amines with alkyl groups of 1 to 6 carbon atoms, piperidine, piperazine, morpholine, pyrrolidine and guanidine.

* * * * *